United States Patent
Testardi (10) Patent No.: US 6,713,765 B2
(45) Date of Patent: Mar. 30, 2004

(54) SCINTILLATING FIBER RADIATION DETECTOR FOR MEDICAL THERAPY

(75) Inventor: Louis R. Testardi, Tallahassee, FL (US)

(73) Assignee: Galileo Scientific, Inc., Tallahassee, FL (US)

( * ) Notice: Subject to any disclaimer, the term of this patent is extended or adjusted under 35 U.S.C. 154(b) by 65 days.

(21) Appl. No.: 10/093,385

(22) Filed: Mar. 11, 2002

(65) Prior Publication Data

US 2003/0168602 A1 Sep. 11, 2003

(51) Int. Cl.$^7$ .............................. G01T 1/29; A61M 36/12
(52) U.S. Cl. ................. 250/363.01; 250/366; 250/458.1
(58) Field of Search ........................... 250/363.01, 366, 250/367, 368, 458.1

(56) References Cited

U.S. PATENT DOCUMENTS

| | | | | |
|---|---|---|---|---|
| 4,598,202 A | * | 7/1986 | Koechner | 250/366 |
| 4,788,436 A | * | 11/1988 | Koechner | 250/485.1 |
| 5,704,890 A | | 1/1998 | Bliss et al. | |
| 5,856,673 A | * | 1/1999 | Ikegami et al. | 250/368 |
| 5,880,475 A | | 3/1999 | Oka et al. | |
| 5,905,263 A | | 5/1999 | Nishizawa et al. | |
| 6,151,769 A | | 11/2000 | Bliss et al. | |
| 6,320,935 B1 | * | 11/2001 | Shinar et al. | 378/119 |
| 2001/0053870 A1 | | 12/2001 | Loffler et al. | |

FOREIGN PATENT DOCUMENTS

| | | |
|---|---|---|
| JP | 10-231663 A1 | 8/1998 |
| JP | 2001-56381 A1 | 2/2001 |
| WO | WO 01/93943 A1 | 12/2001 |
| WO | WO 01/93945 A2 | 12/2001 |

OTHER PUBLICATIONS

U.S. NRC Report NUREG/CR–5223 entitled "ScintillatIng Fiber Detector for In–Vivo Endoscopic Internal Dosimetry", published Oct. 1988.

Phys. Med. Biol., 1992, vol. 37 No. 10, pp. 1883–1900, entitled "Water–equivalent plastic scintillation detectors for high–energy beam dosimetry".

Radiation Oncology, Biology, Physics, vol. 24 Supplement 1, 1992, p. 288, entitled "A Scintillation Detector for the Calibration of Individual Seeds within an Ir–192 Ribbon".

Med. Phys., Mar. 1996, vol. 23 No. 3, pp. 427–434, entitled "Direct reading measurement of absorbed dose rate with plastic scintillators".

Publication: St. Clair, Shaun et al., "An In–Theatre Source Strength Verification System for I–125 Rapid Strand Seeds" (Department of Medical Physics, Yorkshire Centre for Clinical Oncology, Cookridge Hospital, U.K.).

* cited by examiner

Primary Examiner—Constantine Hannaher
Assistant Examiner—Otilia Gabor
(74) Attorney, Agent, or Firm—David A. Testardi

(57) ABSTRACT

A portable dosimetry system measures individual seed strengths of fully loaded multi-seed holders. The system includes a 5 mm diameter scintillating fiber disposed in a groove on a rigid bed. A photomultiplier tube (PMT) is supported on the rigid bed and is coupled to an end surface of the scintillating fiber. Attachments are provided for positioning multi-seed holders adjacent the peripheral surface of the scintillating fiber, and movable shield plates are provided for inhibiting stray radiation (produced by neighboring seeds) from reaching the scintillating fiber. The system is useful for calibrating 100% of the seeds in a holder in less time than it currently takes to calibrate 10% of the seeds in the holder.

40 Claims, 3 Drawing Sheets

SCINTILLATING FIBER RADIATION DETECTOR FOR MEDICAL THERAPY

BACKGROUND OF THE INVENTION

1. Field of the Invention

The present invention pertains to the field of medical radiation dosimetry. More particularly, the present invention pertains to the field of medical radiation dosimetry systems and methods which utilize scintillating fibers for radiation measurement.

2. Description of the Related Art

High energy charged particle and photon radiation can penetrate deeply into solid and liquid matter. Their energy loss leads to ionization along the way. This ionization is useful in many applications including medical therapy. As one example, medical radiation therapy, at Low Dose Rate (LDR) and at High Dose Rate (HDR), has proven beneficial for killing cancer in humans. Its use has also been recently approved by the USA FDA for limited IntraVascular Brachytherapy (IVB) where HDR irradiation of blood vessels opened by balloon angioplasty can often prevent the frequent re-closing of the treated blood vessel (restenosis).

However, current medical radiation dosimetry systems and methods have a number of shortcomings. To begin with, most radioactive seeds for LDR and HDR therapy are not directly measured or verified at the hospital prior to use. Additionally, verification of the seed strengths by the seed maker or supplier or hospital is often carried out on only a statistical sample of about 10% of such seeds because of the long time needed for standard dosimetry.

Applicant is aware of the following related art documents which show the state-of-the-art in e.g. scintillating fiber dosimetry systems, all of which are incorporated by reference herein: McCollough, Kevin P., "A Scintillation Detector for the Calibration of Individual Seeds within an Ir-192 Ribbon", *Radiation Oncology, Biology, Physics,* Volume 24 Supplement 1, 1992, page 288; U.S. Nuclear Regulatory Commission Report NUREG/CR-5223 entitled "Scintillating Fiber Detector for In-Vivo Endoscopic Internal Dosimetry", published October 1988; Beddar, A. S., et al, "Water-equivalent plastic scintillation detectors for high-energy beam dosimetry: I. Physical characteristics and theoretical considerations", *Phys. Med. Biol.,* 1992, Vol. 37 No. 10, pp. 1883–1900; Flühs, D. et al., "Direct reading measurement of absorbed dose rate with plastic scintillators—The general concept and applications to ophthalmic plaque dosimetry", *Med. Phys.* 23 (3), March 1996, pages 427–434; St. Clair, Shaun et al., "An In-Theatre Source Strength Verification System for I-125 Rapid Strand Seeds" (Department of Medical Physics, Yorkshire Centre for Clinical Oncology, Cookridge Hospital, U.K.); U.S. Pat. No. 5,704,890 entitled "Real Time Sensor for Therapeutic Radiation Delivery"; Japanese Published Unexamined Patent Application 10-213663 entitled "Local Dosimeter"; U.S. Pat. No. 5,880,475 entitled "Scintillation Fiber Type Radiation Detector"; U.S. Pat. No. 5,905,263 entitled "Depth Dose Measuring Device"; U.S. Pat. No. 6,151,769 entitled "Method of Making a Scintillator Waveguide"; and Japanese Published Unexamined Patent Application 2001-56381 entitled "Local Radiation Amount Measuring Device and Medical Device Equipped Therewith"; P.C.T. International Patent Application WO 01/93943 entitled "Automated Radioisotope Seed Loader System for Implant Needles"; P.C.T. International Patent Application WO 01/93945 entitled "Automated Radioisotope Seed Cartridge"; U.S. patent application Publication 2001/0053870 entitled "Method for Analyzing Amount of Activity".

Of particular interest, the McCollough article describes a scintillation detector in which a short (3 mm length) scintillating fiber is coupled to a photomultiplier tube (PMT) face. Individual seeds within an Ir-192 ribbon can be scanned while the ribbon is translated under the scintillator.

The two P.C.T. International Patent Applications reveal an automated radioisotope seed loader which includes a "proportional counter type radiation sensor 42" to detect the radiation levels in the seeds as they are loaded from a cartridge to a needle and to verify the radiation strength of the radioisotope seeds.

The U.S. patent application Publication reveals in FIG. 28 a seed-spacer train assembly module which includes a scintillating sheet 209 that emits light when hit by radiation from a seed in a tube 148.

There remains a need for a compact, accurate, and fast-acting scintillating fiber dosimetry system which is particularly adapted for medical applications.

SUMMARY OF THE INVENTION

It is a first object of the invention to provide a compact, accurate, and fast-acting scintillating fiber dosimetry system which is particularly adapted for medical applications.

It is another object of the invention to provide a scintillating fiber dosimetry system and associated method which can be used at a hospital or radiation treatment facility for Quality Assurance (QA) in verifying radiation dose levels.

It is a further object of the invention to provide a scintillating fiber dosimetry system which is particularly adapted to measure the radiation produced by a number of seeds pre-loaded within a needle or cartridge.

It is a still further object of the invention to provide a scintillating fiber dosimetry system which is useful for calibrating 100% of the seeds in a holder in less time than it currently takes to calibrate 10% of the seeds in the holder.

It is a still further object of the invention to provide a scintillating fiber dosimetry system which is useful for detecting the spacers between the seeds in a pre-loaded seed needle or cartridge.

In one respect the invention relates to a dosimetry system comprising: a rigid structure; a scintillating fiber mounted on the rigid structure in a substantially relatively immovable manner, the scintillating fiber having a cylindrical peripheral surface and first and second end surfaces; a light intensity measuring device attached to the rigid structure in a substantially relatively immovable manner; coupling means for optically coupling the first end surface of the scintillating fiber to an active portion of the light intensity measuring device; wherein the light intensity measuring device produces an output signal in accordance with an amount of light generated by the scintillating fiber; and wherein the scintillating fiber is mounted on the rigid structure in such a manner that a longitudinal axis of the scintillating fiber extends in a direction away from the active portion of the light intensity measuring device, with a distance between the active portion of the light intensity measuring device and the second end surface of the scintillating fiber being between substantially 15 mm and substantially 200 mm, and wherein a portion of the cylindrical peripheral surface of the scintillating fiber is unshielded and accessible; and wherein radiation measurement is carried out adjacent the accessible portion of the cylindrical peripheral surface of the scintillating fiber.

DETAILED DESCRIPTION OF THE PREFERRED EMBODIMENTS

Figure 1:
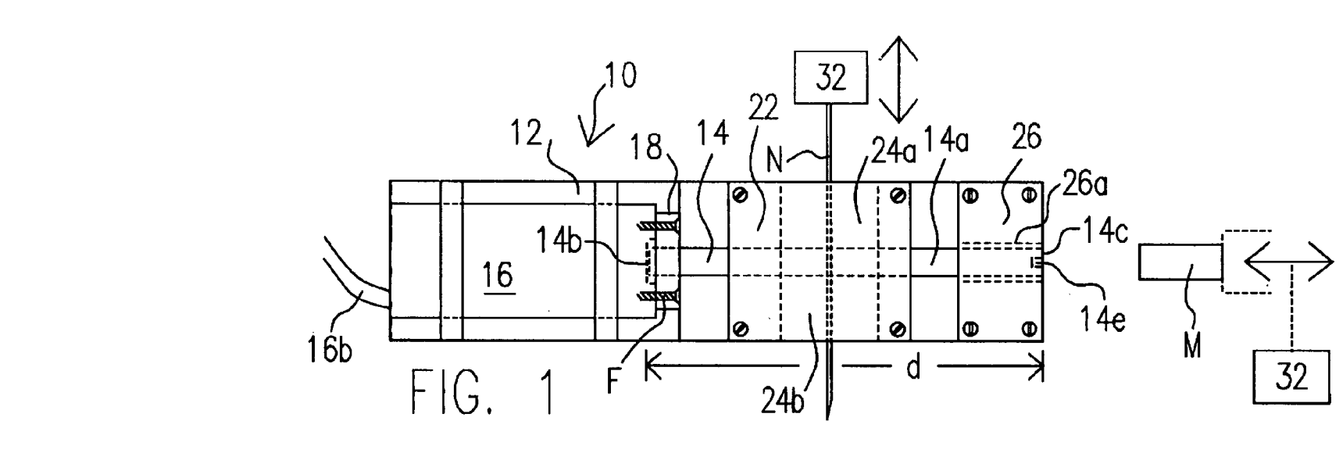
FIG. 1 is a top representation of a scintillating fiber dosimeter according to a preferred embodiment of the invention.
Figure 2:
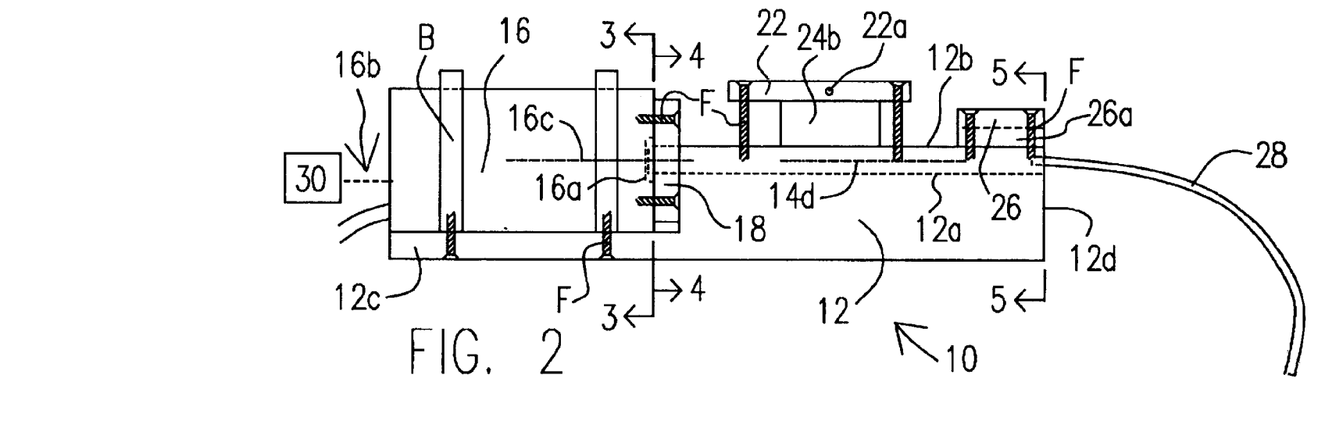
FIG. 2 is a side representation of the scintillating fiber dosimeter shown in FIG. 1.
Figures 3, 4, 5:
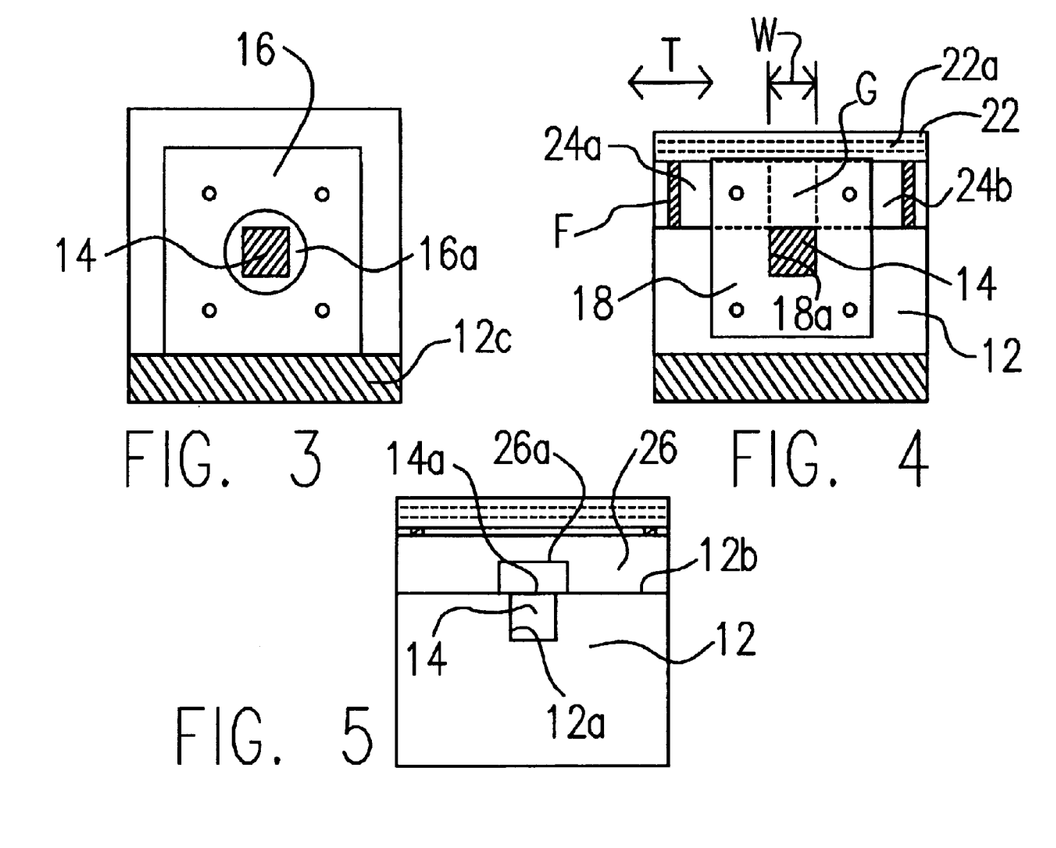
FIG. 3 is a cross-sectional representation of the scintillating fiber dosimeter of FIGS. 1 and 2 taken along lines 3—3 in FIG. 2 and looking in the direction toward the photomultiplier tube.
FIG. 4 is a cross-sectional representation of the scintillating fiber dosimeter of FIGS. 1 and 2 taken along lines 4—4 in FIG. 2 and looking in the direction away from the photomultiplier tube.
FIG. 5 is a representation of the scintillating fiber dosimeter of FIGS. 1 and 2 taken along lines 5—5 in FIG. 2 and looking in the direction toward the photomultiplier tube.

Referring now to FIGS. 1 to 5, there is shown a scintillating fiber dosimeter, indicated generally at 10, which includes a rigid structure in the form of a bed 12 having a groove 12a formed therein (see FIG. 5). The bed 12 is made from aluminum or other suitably rigid material (e.g. metal, plastic) and has a length of between about 75 mm and 260 mm, with about 95 mm to 170 mm being preferred, and about 135 mm to 170 mm being most preferred. In the preferred embodiment, the groove 12a is square in cross-section, having width of substantially 5 mm and a depth of substantially 5 mm. As shown in FIG. 5, the groove 12a is formed in an otherwise planar top surface 12b of the bed. However, other groove cross-sections and sizes may also be employed.

Disposed within the bed groove 12a is a conventional scintillating fiber 14 (for example, Bicron BCF-10). The scintillating fiber 14 is mounted (or supported) on the rigid bed 12 in a substantially relatively immovable manner by means hereinafter described. The scintillating fiber 14 is characterized by a cylindrical peripheral surface 14a, a first end surface 14b, and second end surface 14c.

In the preferred embodiment, the scintillating fiber 14 has a substantially or generally square cross-section of approximately 5 mm on a side. However, it is envisioned that other scintillating fiber cross-sectional shapes (e.g. circular) and dimensions (e.g. diameters) may also be employed. For example, scintillating fibers with cross-sectional diameters as small as 0.25 mm may be employed.

Because in the preferred embodiment a square cross-section scintillating fiber 14 is employed, the peripheral surface 14a of the scintillating fiber 14 is a square cylindrical surface that closely matches the depth and width of the bed groove 12. As a result, a top portion (or side) of the cylindrical peripheral surface 14a of the scintillating fiber 14 (e.g. as shown in FIGS. 1 and 5) becomes substantially flush with the top planar surface 12b of the bed 12.

A first end 14b of the scintillating fiber 14 is coupled to a light intensity measuring device 16. In the preferred embodiment, the light intensity measuring device 16 comprises a small, portable, battery-powered photomultiplier tube (PMT) having a length of approximately 60 mm. Such a PMT is made, for example, by Hamamatsu Photonics (Japan). The PMT is rigidly attached (or fixed) to a tail portion 12c of the bed 12 (in a substantially relatively immovable manner) by means of suitable threaded fasteners F (FIG. 2) that engage U-shaped brackets B which surround and clamp the PMT. The PMT (or other light intensity measuring device 16) includes an active portion or face 16a (having a circular diameter of 8 to 9 mm as shown in FIG. 3) which closely confronts/abuts the first end surface 14b of the scintillating fiber 14. The active portion or face 16a of the PMT receives the light emanating from the first end surface 14b of the scintillating fiber, and the PMT produces an output signal in accordance with an amount of light generated by the scintillating fiber 14. Electrical lines 16b are connected to the PMT to provide power to the system (+12 V/–12 V) and to transmit the output signal of the PMT to output circuitry indicated generally at 30. In the simplest form, the output circuitry 30 may comprise a portable voltage reading multimeter. In more advanced systems, the output circuitry 30 may include an analog-to-digital converter which receives the analog output signal of the PMT and converts it to digital form for subsequent input to and processing in a digital signal processor (which may be embodied in a portable laptop or desktop computer, not shown), and the digital signal processor preferably includes software for viewing and storing the measurement results. In the preferred embodiment, the PMT has a minimum sensitivity of ~$10^{10}$ V/Optical-Watt-Input-@400 nm, a wide dynamic range, and bandwidth >10 kHz to allow measurements of rapid dose-rate changes, and the output signal voltage of the PMT is measured at 100 microvolt resolution, or better. The minimum Input-Light Noise Equivalent Power (NEP) for medical therapy is $10^{-15}$ Watts, which is also satisfied by the PMT.

An optical fiber adapter 18 is employed to mechanically connect the scintillating fiber 14 to the light intensity measuring device 16 in such a manner that the first end surface 14b of the scintillating fiber is optically coupled to the active portion or face 16a of the PMT. The adapter 18 is rigidly attached to the front end of the light intensity measuring device 16 by means of suitable threaded fasteners F (FIG. 1). The adapter 18 takes the form of a rectangular plate 18 having a 5 mm square hole 18a punched through a middle portion thereof. When the adapter 18 is mounted to the PMT, the center of the square hole is coextensive both with the center of the square groove 12a and with the longitudinal axis 16c of the light intensity measuring device 16.

To mechanically connect the scintillating fiber to the adapter plate 18, the scintillating fiber 14 is inserted into the square hole 18a of the adapter plate 18 until first end surface 14b of the scintillating fiber 14 confronts or abuts the active portion or face 16a of the PMT. (For example, there may be a 1 mm space between the active portion or face 16a of the PMT and the first end surface 14b of the scintillating fiber 14 when the scintillating fiber 14 is inserted into the square hole 18a of the adapter plate 18.) The square hole 18a snugly receives and frictionally holds (e.g. substantially immovably relatively to the bed, during use of the dosimeter) a portion of the cylindrical peripheral surface 14a of the scintillating fiber 14 adjacent the first end surface 14b. This optically couples the first end surface 14b of the scintillating fiber 14 to the active portion or face 16a of the PMT. In this condition, when the light intensity measuring device 16 is attached to the bed 12 and the scintillating fiber 14 is seated within the groove 12a, the central longitudinal axis 14d (FIG. 2) of the scintillating fiber 14 becomes aligned (e.g. coextensively) with the axis 16c of the of the PMT.

Preferably, the second end surface 14c of the scintillating fiber 14 is disposed approximately in the portion of the bed groove 12a which is most distal from the PMT. For example, the second end surface 14c of the scintillating fiber 14 may be approximately or substantially flush with the vertical end surface 12d of the rigid bed 12. It is presently preferred that the longitudinal axis 14d of the scintillating fiber 14 extends in a direction away from the active portion or face 16a of the light intensity measuring device, with a distance "d" between the active portion or face 16a of the light intensity measuring device 16 and the second end surface 14c of the scintillating fiber 14 being between substantially 15 mm and substantially 200 mm. In the preferred embodiment shown in FIGS. 1 and 2, this distance "d" is also approximately or substantially equal to both the length of the scintillating fiber 14 (e.g. minus the distance of any small gap that may exist between the active portion or face 16a of the PMT and the first end surface 14b of the scintillating fiber 14), and the distance between the active portion or face 16a of the PMT and the vertical end surface 12d of the rigid bed 12. While in a broad aspect of the invention, this distance "d" between the active portion or face 16a of the light intensity measuring device 16 and the second end surface 14c of the scintillating fiber 14 may be substantially between 15 mm and 200 mm (or more), a preferred distance range for "d" is substantially between 30 mm and 110 mm, with the most preferred distance range being substantially between 75 mm to 110 mm.

It will thus be seen that, due to the length of the bed 12 and due to the distance "d" which separates the active portion or face 16a of the PMT and the second end surface 14c of the scintillating fiber, a portion of the cylindrical peripheral surface 14a of the scintillating fiber 14 (e.g. the top side of the scintillating fiber to the right of the adapter plate 18 in FIGS. 1 and 2) is unshielded (i.e. from radiation) and is accessible (i.e. to permit a radiation source to be positioned adjacent to the cylindrical peripheral surface 14a). Radiation measurement is therefore preferably carried out adjacent to this accessible portion of the cylindrical peripheral surface 14a of the scintillating fiber 14.

Two attachment pieces are securely fixed to the rigid bed 12 in the vicinity of the unshielded and accessible portion of the cylindrical peripheral surface 14a of the scintillating fiber 14.

The first attachment piece 22 comprises a plate (made from plexiglass or the like) having a thickness (or height) of approximately 3 mm, a length (in the axial direction of the scintillating fiber 14) of approximately 40 mm, and a width approximately equal to the transverse width of the rigid bed 12 (e.g. 25 mm to 38 mm). A hole 22a is provided completely through the first attachment piece 22. When the first attachment piece 22 is fastened to the rigid bed 12 by means of threaded fasteners F (FIG. 2) so as to overlie the scintillating fiber 14, the hole 22a is spaced above and extends transversely (i.e. perpendicularly or orthogonally) to the longitudinal axis 14d of the scintillating fiber 14.

The hole 22a has a diameter adapted to receive, position, and guide a needle N loaded with a plurality of radioactive seeds (as are often employed in brachytherapy treatment). The hole 22a guides the needle horizontally in a direction transverse to the longitudinal direction 14d of the scintillating fiber, and the hole diameter may be approximately 1.0 to 1.2 mm, or whatever diameter will provide a sliding fit for the needle N without significant lateral play.

Interposed and clamped between the first attachment plate 22 and the rigid bed 12 are two shield plates 24a, 24b (collectively referred to as 24) which are each adjustably positioned on opposite transverse sides of the scintillating fiber 14 so that an adjustable gap (G in FIG. 4) can be formed between the shield plates 24 above the scintillating fiber. The shield plates 24 are preferably > (120/SpecificGravity) mm in each direction. In the preferred embodiment, the shielding plates 24 are made from tungsten (SpecificGravity is ~20), and have a thickness (height) of 7 mm, a length (in the axial direction of the scintillating fiber 14) of approximately 18 mm, and a transverse width of approximately 12 mm. The purpose of the shield plates 24 is to inhibit stray radiation (e.g. from neighboring seeds inside the needle) from reaching the scintillating fiber.

To adjust the transverse position of the shield plates 24, the threaded fasteners F which attach the first attachment plate to the rigid bed 12 are temporarily loosened, the plates 24a, 24b are slid toward or away from each other (in the directions "T" labelled in FIG. 4) until the desired gap G is formed between them above the scintillating fiber 14, and then the threaded fasteners F are retightened to thereby frictionally clamp and lock the shield plates in position with the gap G having the desired transverse width. Usually, the desired transverse width W of the gap will be approximately equal to the seed length which characterizes the particular radioactive seeds loaded into the needle. (The seeds are loaded lengthwise end-to-end in the needle, and spacers may be employed between adjacent seeds.)

The second attachment piece 26 comprises a plate (made from plexiglass or the like) having a thickness (or height) of approximately 6 mm, a length (in the axial direction of the scintillating fiber 14) of approximately 15 mm, and a width approximately equal to the transverse width of the rigid bed 12 (e.g. 28 mm to 35 mm). A channel 26a (FIG. 5) is provided in the bottom of the second attachment piece 26. When the second attachment piece 26 is fastened to the rigid bed 12 by means of threaded fasteners F (FIG. 2) so as to overlie the scintillating fiber 14, the channel 26a is disposed above and extends parallel to the longitudinal axis 14d of the scintillating fiber 14.

The channel 26a can be just over 3 mm deep (or high), and just over 7 mm wide (in the direction transverse to the longitudinal axis 14d of the scintillating fiber 14); it extends the entire length of the second attachment piece 26. These dimensions are non-limiting, and the channel may have other functional sizes as well.

In particular, the channel 26a is sized to slidably receive, position, and guide that portion of a conventional Mick cartridge M (or other cartridge) which is loaded with a plurality of seeds. The channel 26a guides the Mick cartridge M in a direction parallel to the longitudinal axis of the scintillating fiber. The seed-loaded portion (shown in solid lines) of the Mick cartridge M is substantially 15 mm long, 3 mm high and 7 mm wide. It houses seeds that are approximately 5 mm long and 0.8 mm in diameter. The axes of the seeds extend parallel to the width of the cartridge, and the seeds are disposed side-to-side, and spacers may be employed between adjacent seeds.

A third attachment in the form of an additional thin, flexible scintillating fiber 28 is also provided for the scintillating fiber dosimeter 10. The additional scintillation fiber 28 may have a sub-mm round cross-section and may have a length up to about 1 meter. The additional scintillating fiber 28 is directly optically (and mechanically) coupled to the scintillating fiber 14 e.g. by providing the second end surface 14c of the scintillating fiber 14 with a small, precision hole 14e (FIG. 1) and press-fitting or adhering the additional scintillating fiber 28 into the small, precision hole 14e.

Figure 6:
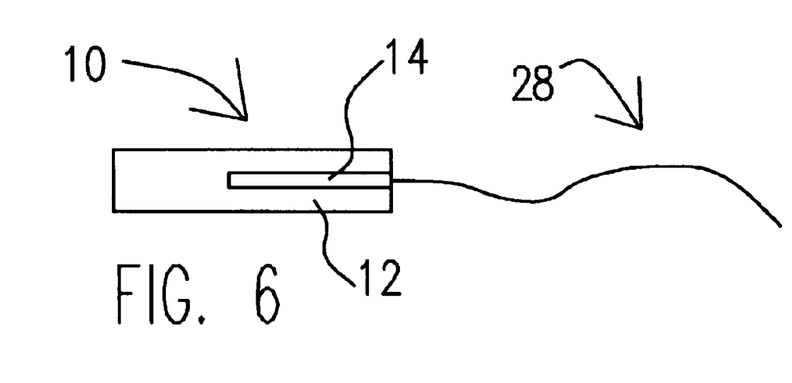
FIG. 6 is a schematic representation of the scintillating fiber dosimeter of FIGS. 1 and 2 cooperating with a thin, flexible additional scintillating fiber.

FIG. 6 shows the schematical relationship between the rigid bed 12, the scintillating fiber 14, and the additional scintillating fiber 28. As will be apparent, the flexibility and length of the additional scintillating fiber 28 facilitate remote access for radiation measurement in otherwise hard-to-reach locations. That is, the additional scintillating fiber 28 can be manipulated and guided into the hard-to-reach location, and scintillating light produced by the additional scintillating fiber 28 is piped from the additional scintillating fiber, through the scintillating fiber 14 to the active portion or face 16a of the PMT.

It is noted that all surfaces of the scintillating fibers 14, 28 not intended to transmit light (e.g. all surfaces except the first end surface 14b of the scintillating fiber 14 and the surfaces which optically couple the scintillating fiber 14 with the additional scintillating fiber 28), as well as all mechanical joints in the scintillating fiber dosimeter 10 (e.g. the joint between the PMT and the adapter plate 18 and the joint between the adapter plate 18 and the scintillating fiber 14) are shielded from the adverse effects of ambient light and from light leaks by any conventional or known means. For example, sequential layers of aluminum foil and black electrical tape may be placed over the bed groove 12a to cover the scintillating fiber 14, and also around the adapter plate joints and exposed fiber ends. An extramural absorber coating may also be applied to the peripheral wall of either or both scintillating fibers. In the case where the additional scintillating fiber 28 is not employed, the second end surface 14c of the scintillating fiber 14 including the hole 14e can be covered by aluminum foil and black electrical tape.

Figure 7:
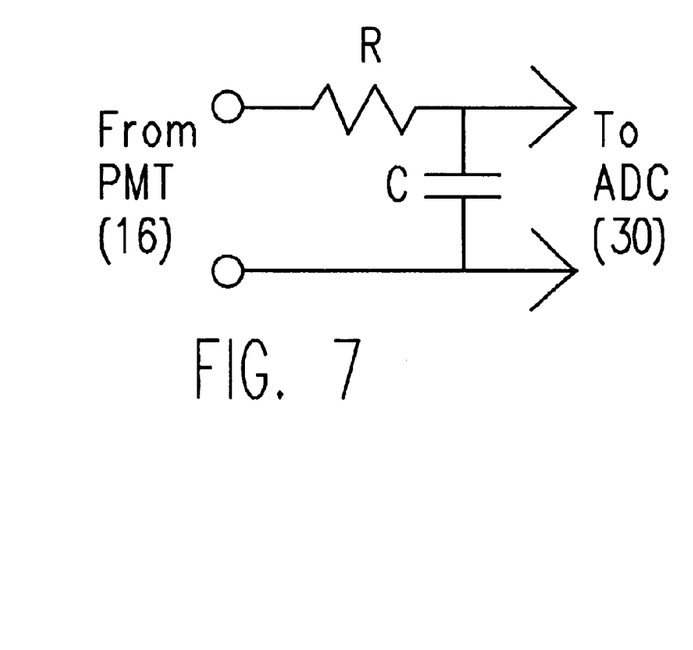
FIG. 7 is a schematic representation of the output circuitry attached to the photomultiplier tube.

FIG. 7 is a schematical representation of an integrator input circuit (IIC) which is preferably interposed between the differential voltage signal outputs of the PMT and the analog-to-digital converter (ADC) of the output circuitry 30 for filtering or smoothing high-frequency variations which may be included in the PMT output signal. The IIC includes a resistance R (e.g. 15 k$\Omega$) in one of the signal lines from the PMT to the ADC, and a capacitance C (e.g. 10 $\mu$F) downstream of the resistance R bridging the two signal lines from the PMT to the ADC. As will be understood, the IIC functions as a low-pass filter having an RC response time of 0.15 seconds and a cutoff frequency (−3 dB) of $(2\pi RC)^{-1}$. (The RC response time of the IIC should fall between 0.1 and 1.0 seconds, with 0.15 to 0.2 seconds being preferred.)

Use of the scintillating fiber dosimeter will be described next.

In the case where it is desired to measure the radiation produced by a number of seeds pre-loaded within a brachytherapy needle, the threaded fasteners F which attach the first attachment piece to the rigid bed 12 are first loosened and the transverse gap G between the shield plates 24a, 24b is adjusted so as to be substantially equal to the seed length (e.g. 5 mm) of the seeds loaded in the needle to be tested. The threaded fasteners F are then retightened to clamp and lock the shield plates 24a, 24b in place. Next, the loaded needle N is inserted transversely into the hole 22a provided in the first attachment piece 22, and it is displaced linearly within the hole 22a (as indicated by the double-headed arrow in FIG. 1) so that each and every one of the seeds in the needle passes, sequentially one-by-one, over the gap G and thus over the cylindrical peripheral surface 14a of the scintillating fiber 14. As each individual seed passes over the gap G, radiation from the individual seed produces scintillating light in the scintillating fiber 14 (the radiation from neighboring seeds being shielded by the adjusted shield plates 24a, 24b). This light is measured by the PMT (measurement times can be 2 to 5 seconds per seed plus spacer, or faster, to allow for signal integration), and the PMT produces a voltage output which gives an indication of the radiation dose-rate produced by or activity of the individual seed.

In the case where it is desired to measure the radiation produced by a number of seeds pre-loaded within a Mick cartridge, the loaded Mick cartridge M is inserted longitudinally into the channel 26a provided in the second attachment piece 26 (i.e. with the length of the Mick cartridge seed loaded portion disposed parallel to the central longitudinal axis 14d of the scintillating fiber 14), and it is displaced linearly into the channel (as indicated by the double-headed arrow in FIG. 1) so that all of the seeds overlie the cylindrical peripheral surface 14a of the scintillating fiber 14. Radiation from all of the seeds in the Mick cartridge produces scintillating light in the scintillating fiber 14. This light is measured by the PMT, and the PMT produces a voltage output which gives an indication of the radiation dose-rate produced by or total activity of the seeds in the Mick cartridge.

If desired, it may be possible to measure individually the seeds loaded within a Mick cartridge by providing between the scintillating fiber 14 and the second attachment piece 26 supplemental shield plates (not shown) establishing a narrow sensing gap (e.g. 0.8 mm wide) that is aligned with the in-cartridge seed orientation. The supplemental shield plates would then be effective to block radiation from neighboring seeds in the Mick cartridge, and the Mick cartridge could be displaced linearly so that each and every one of the seeds in the cartridge passes, sequentially one-by-one, over the narrow sensing gap. However, due to the close seed spacing in a Mick cartridge, a mechanical displacement method may also be necessary to achieve sufficient precision for accurate individual seed measurement.

In either the case of pre-loaded needle measurement or pre-loaded Mick cartridge measurement, measurements can optionally be made while preserving polymer-bag sterility of the needle of cartridge, if the hole 22a or channel 26a is configured to additionally receive the bag which surrounds the needle or cartridge bag. The linear displacement of the needle or Mick cartridge in the hole 22a or channel 26a can be effected by the hand of an operator. However in order to reduce the possibility of measurement error it is presently preferred to employ "motive means" in the form of a linear electric or fluid actuator to non-manually displace the needle or cartridge. The motive means is indicated generally in FIG. 1 at 32. In the most preferred embodiment, the motive means comprises a D.C. electric motor (coupled to a motion conversion device such as a screw-nut actuator) which runs off the same voltage supply that powers the PMT. The motive means 32 (which may be attached to the rigid bed 12) moves the needle or Mick cartridge at a substantially constant linear speed (e.g. on the order of 5 seconds per centimeter) as it is guided within the hole 22a or channel 26a during radiation measurement procedures. It is envisioned that a displacement indicating output of the motive means may be utilized by a digital signal processor in the output circuitry 30 to log the actual positions of the seeds in the needle or cartridge as the needle or cartridge is undergoing measurement.

Nonradioactive spacers are often placed between radioactive seeds to provide the proper radiation distribution in medical therapy. These spacers can be readily detected when a seed-containing needle is slid over the scintillating fiber since the signal will be at a peak when a seed passes, and the signal will be at a valley when the spacer passes. The ratio of the signal peak width to the valley width will give the spacer length in terms of the seed length. In this way, a missing, or an extra spacer, can be readily detected.

This method will also apply to the Mick cartridge when used in conjunction with the shown embodiment, except that signal steps (instead of signal peaks and valleys) will be observed.

In the case where it is desired to measure the radiation produced by a single seed (so called "measure-seed-by-swiping"), neither the first attachment piece nor the second attachment piece is required. The seed is manually manipulated (e.g. with tweezers) so as to be adjacent the cylindrical peripheral surface 14a of the scintillating fiber. For a "High Dose Rate" source (such as an Ir-192 seed), the seed can be held up to a foot from the cylindrical peripheral surface of the scintillating fiber 14a. For a "Low Dose Rate" source (such as an I-125 seed), the seed should be located within 10 mm or a few 10s of mm from the cylindrical peripheral surface 14a of the scintillating fiber 14 for most accurate measurements. Radiation from the seed produces scintillating light in the scintillating fiber 14. This light is measured by the PMT, and the PMT produces a voltage output which gives an indication of the radiation dose-rate produced by or total activity of the seed.

[As used herein, the phrase "adjacent . . . the cylindrical peripheral surface", when used in conjunction with the radiation source location, implies a proximity to the scintillating fiber which yields accurate radiation measurements. In virtually all cases of medical radiation therapy measurement, a proximity of about 10 mm or less will yield accurate radiation measurements, but this particular distance by no means limits applicant's invention.]

In the case where it is desired to measure radiation using the additional scintillating fiber 28, the fiber is manually or automatically manipulated or translated so as to be adjacent the radiation source. For example, the additional scintillating fiber 28 can be easily introduced into most seed-loading devices or procedures so that its tip or periphery is adjacent to the radiation source. Radiation from the radiation source produces scintillating light in the scintillating fiber 28 which is piped through the scintillating fiber 14 to the active portion or face 16a of the PMT. This piped light is measured by the PMT, and the PMT produces a voltage output which gives an indication of the radiation dose-rate produced by or total activity of the radiation source. In conjunction with the translation of the additional scintillating fiber 28 relative to a radiation source, a Displacement Difference Dosimetry (DDD) signal processing method is preferably employed by the digital signal processor in the output circuitry 30 in order to provide fine spatial resolution and to minimize the adverse efects of Cerenkov light on the measurement accuracy scintillating fiber dosimeter 10. A separate U.S. patent application directed to the DDD method entitled "RADIATION MEASUREMENT WITHIN THE HUMAN BODY", Ser. No. 10/084,163, was filed on Feb. 28, 2002 by the inventor hereof and is incorporated by reference herein.

A Quality Assurance (QA) advantage of scintillating fiber HDR dosimetry results from its fast response. Since HDR dose-rates are up to $10^4$ greater than LDR dose-rates, the signal strength produced by the PMT can be up to $10^4$ greater, and the signal averaging time (to allow for signal integration) can thus be $\sim 10^4$ shorter than for LDR sources. However, this requires a light intensity measuring device with a $10^4$ dynamic range and a 10 kHz bandwidth if the same detector is used. A $10^4$ dynamic range and a 20 kHz bandwidth are available with compact, battery-operated PMT modules. By way of example, measurements of a moving HDR source (typically traveling in a catheter at 300 mm/sec) using the scintillating fiber dosimeter are possible without interruption.

Other specific QA examples are provided below:

Using the Maximum Hold feature of some hand-held multimeters, or an ADC with a computer, the scintillating fiber dosimeter can measure the activity from an HDR source, moving in a catheter, on entering and leaving the patient. This can provide a QA alert if even <1% of the source is left in the catheter or patient after irradiation.

Using an ADC with a computer, or a handheld oscilloscope, the non-uniformity of dose-rate of a (HDR) seed-train moving in a catheter, or its off-centering condition, can be determined. Only a single flexible scintillating fiber (such as the additional scintillating fiber 28 in the preferred embodiment) spirally wrapped around a tube holding the catheter is needed. In-Vivo tracking of afterloader prostate irradiation by inserting a scintillating fiber in one of the applicator tubes is relatively easy.

Measurement of LDR radiation from radiopharmaceuticals circulating in the blood (to determine biological half-life) can be effected with the additional scintillating fiber 28 (e.g., taped on the skin). Since the dosimeter is battery-operated and portable, it is easily attached to the patient. Data storage, PC communication and software can be easily obtained. This application will enhance dosimetry for the precise and localized delivery and history of radiopharmaceuticals in the treatment of disease without discomfort to the patient, and provide an accurate measure of the biological half-life of the radio-nuclide in the body.

For LDR measurements, the measurement precision for inter-comparison of seed activities is about 2% with the scintillating fiber dosimeter 10. This will also be the accuracy, if one calibrated seed is used, and calibration of the dosimeter output is performed.

The responsivity of a prototype Scintillating Fiber/PMT Dosimeter, with PMT Gain $\sim 7*10^{10}$ V/Optical-Watt-at-400 nm-Input, is 120 mV/mCi for I-125 in single seeds at 5.5 mm from the scintillating fiber center. For the dosimeter, this responsivity will vary approximately as 1/(source-to-fiber distance) for source-to-fiber distance which is much less than the scintillating fiber length. This value has allowed economical multimeters or ADC's for final digital measurement. Because of the linear response, accurate relative calibration can be achieved without absolute calibration, that is, without a knowledge of the voltage responsivity value.

As used herein, the term "cylindrical" encompasses not only circular cylinders, but also other polygonal and closed-form cylinders (e.g. square cylinders). The phrase "relatively immovable manner" when used to describe the support of one part upon another or the attachment of two parts together signifies that during normal use of the scintillating fiber dosimeter (e.g. during a measuring procedure), the two parts do not move significantly relative to each other (though both can be part of a portable system). For example, the scintillating fiber 14 does not move significantly within the bed groove 12a during a measurement procedure (i.e. it is held by its own gravitational and the groove's reaction forces, by the friction created between the adapter plate hole 18a and the scintillating fiber's cylindrical periphery 14a, and by the aluminum foil and black electrical adhesive tape which optionally overlies the bed groove 12a), and the PMT does not move significantly relatively to the bed 12 (being fixed thereto by the fasteners F and the U-shaped mounting brackets B).

While the above invention has been described with certain particularity, it is not meant to be limited to the above described preferred embodiments. For example, the scintillating fiber 14 may be a bundle of scintillating fibers which each have a smaller transverse size. The scintillating fiber 14 may be a composite optical/scintillating fiber, with the scintillating fiber at the tip of the optical fiber, and with both fibers being supported (or mounted) by the bed groove 12a. The bed groove 12a may take forms other than a square or rectangular groove (e.g. matching the shape of the bottom and/or sides of the scintillating fiber 14). Therefore, the invention will encompass the preferred embodiments described above as well as any modifications thereof which will fall within the scope of the appended claims.

I claim:

1. A dosimetry system for measuring radiation produced by radioactive seeds, comprising:
   a rigid structure;
   a scintillating fiber mounted on the rigid structure in a substantially relatively immovable manner, the scintillating fiber having a cylindrical peripheral surface and first and second end surfaces, the scintillating fiber being substantially immovable relative to the rigid structure;
   a light intensity measuring device attached to the rigid structure in a substantially relatively immovable manner;
   coupling means for optically coupling the first end surface of the scintillating fiber to an active portion of the light intensity measuring device;
   wherein the light intensity measuring device produces an output signal in accordance with an amount of light generated by the scintillating fiber; and
   wherein the scintillating fiber is mounted on the rigid structure in such a manner that a longitudinal axis of the scintillating fiber extends in a direction away from the active portion of the light intensity measuring device, with a distance between the active portion of the light intensity measuring device and the second end surface of the scintillating fiber being between substantially 15 mm and substantially 200 mm, and wherein a portion of the cylindrical peripheral surface of the scintillating fiber is both unshielded from radiation and accessible; and wherein radiation measurement is carried out adjacent the unshielded and accessible portion of the cylindrical peripheral surface of the scintillating fiber.

2. The dosimetry system as recited in claim 1, wherein the coupling means comprises an optical fiber adapter which is fixed to the light intensity measuring device and which snugly receives a portion of the cylindrical peripheral surface of the scintillating fiber adjacent to the first end surface.

3. The dosimetry system as recited in claim 2, further comprising an attachment piece which is fixed to the rigid structure and which includes an opening therein adjacent the unshielded and accessible portion of the cylindrical peripheral surface of the scintillating fiber for receiving and positioning a multi-seed holder relative to the scintillating fiber during radiation measurement.

4. The dosimetry system as recited in claim 2, wherein a cross-sectional dimension of the scintillating fiber is approximately 5 mm.

5. The dosimetry system as recited in claim 2, wherein the rigid structure is a rigid bed, and wherein the light intensity measuring device is attached to a tail portion of the rigid bed.

6. The dosimetry system as recited in claim 1, wherein the light intensity measuring device comprises a battery-powered photomultiplier tube.

7. The dosimetry system as recited in claim 6, further comprising an attachment piece which is fixed to the rigid structure and which includes an opening therein adjacent the unshielded and accessible portion of the cylindrical peripheral surface of the scintillating fiber for receiving and positioning a multi-seed holder relative to the scintillating fiber during radiation easurement.

8. The dosimetry system as recited in claim 1, wherein the output signal from the light intensity measuring device is fed through an integrator circuit to an analog-to-digital converter.

9. The dosimetry system as recited in claim 1, wherein the distance between the active portion of the light intensity measuring device and the second end surface of the scintillating fiber is between substantially 30 mm and substantially 110 mm.

10. The dosimetry system as recited in claim 9, wherein the rigid structure is a rigid bed, and wherein the scintillating fiber is disposed within a groove on the rigid bed.

11. The dosimetry system as recited in claim 10, wherein the light intensity measuring device comprises a battery-powered photomultiplier tube which is fixed to the rigid bed.

12. The dosimetry system as recited in claim 1, wherein the distance between the active portion of the light intensity measuring device and the second end surface of the scintillating fiber is between substantially 75 mm and substantially 110 mm.

13. The dosimetry system as recited in claim 12, wherein the rigid structure is a rigid bed, and wherein the scintillating fiber is disposed within a groove on the rigid bed.

14. The dosimetry system as recited in claim 13, wherein the light intensity measuring device comprises a battery-powered photomultiplier tube which is fixed to the rigid bed.

15. The dosimetry system as recited in claim 12, further comprising an attachment piece which is fixed to the rigid structure and which includes an opening therein adjacent the unshielded and accessible portion of the cylindrical peripheral surface of the scintillating fiber for receiving and positioning a multi-seed holder relative to the scintillating fiber during radiation measurement.

16. The dosimetry system as recited in claim 1, wherein the rigid structure is a rigid bed, and wherein the light intensity measuring device is attached to a tail portion of the rigid bed.

17. A dosimetry system for measuring radiation produced by radioactive seeds comprising:
   a rigid structure;
   a scintillating fiber mounted on the rigid structure in a substantially relatively immovable manner, the scintillating fiber having a cylindrical peripheral surface and first and second end surfaces;
   a light intensity measuring device attached to the rigid structure in a substantially relatively immovable manner;
   coupling means for optically coupling the first end surface of the scintillating fiber to an active portion of the light intensity measuring device;
   wherein the light intensity measuring device produces an output signal in accordance with an amount of light generated by the scintillating fiber;

wherein the scintillating fiber is mounted on the rigid structure in such a manner that a longitudinal axis of the scintillating fiber extends in a direction away from the active portion of the light intensity measuring device, with a distance between the active portion of the light intensity measuring device and the second end surface of the scintillating fiber being between substantially 15 mm and substantially 200 mm, and wherein a portion of the cylindrical peripheral surface of the scintillating fiber is unshielded from radiation and accessible; wherein radiation measurement is carried out adjacent the accessible portion of the cylindrical peripheral surface of the scintillating fiber; and wherein the dosimetry system further comprises:

an attachment piece which is fixed to the rigid structure and which includes an opening therein adjacent the accessible portion of the cylindrical peripheral surface of the scintillating fiber for receiving and positioning a multi-seed holder relative to the scintillating fiber during radiation measurement.

18. The dosimetry system as recited in claim 17, wherein the opening is a hole which extends transversely to the longitudinal axis of the scintillating fiber.

19. The dosimetry system as recited in claim 18, wherein the hole is dimensioned to receive, position, and guide a needle containing a plurality of seeds, the needle being guided in a direction transverse to the longitudinal axis of the scintillating fiber.

20. The dosimetry system as recited in claim 19, wherein motive means are provided for moving the needle in the direction transverse to the longitudinal axis of the scintillating fiber.

21. The dosimetry system as recited in claim 20, wherein the motive means comprises an electrical actuator.

22. The dosimetry system as recited in claim 18, wherein a shielding means is disposed between the hole in the attachment piece and the rigid structure for inhibiting stray radiation from reaching the scintillating fiber.

23. The dosimetry system as recited in claim 22, further including:

means for adjustably positioning the shielding means relative to the attachment piece; and means for locking the shielding means in place relative to the attachment piece.

24. The dosimetry system as recited in claim 23, wherein the locking means comprises at least one threaded fastener which clamps the shielding means in place.

25. The dosimetry system as recited in claim 17, wherein the opening is a channel which extends substantially parallel to the longitudinal axis of the scintillating fiber.

26. The dosimetry system as recited in claim 25, wherein the channel is dimensioned to receive, position, and guide a Mick cartridge containing a plurality of seeds, the Mick cartridge being guided in a direction substantially parallel to the longitudinal axis of the scintillating fiber.

27. The dosimetry system as recited in claim 26, wherein motive means are provided for moving the Mick cartridge in the direction substantially parallel to the longitudinal axis of the scintillating fiber.

28. The dosimetry system as recited in claim 27, wherein the motive means comprises an electrical actuator.

29. A dosimetry system for measuring radiation for medical applications comprising:

a rigid structure;

a scintillating fiber mounted on the rigid structure in a substantially relatively immovable manner, the scintillating fiber having a cylindrical peripheral surface and first and second end surfaces;

a light intensity measuring device attached to the rigid structure in a substantially relatively immovable manner;

coupling means for optically coupling the first end surface of the scintillating fiber to an active portion of the light intensity measuring device;

means for shielding the scintillating fiber from ambient light;

wherein the light intensity measuring device produces an output signal in accordance with an amount of light generated by the scintillating fiber;

wherein the scintillating fiber is mounted on the rigid structure in such a manner that a longitudinal axis of the scintillating fiber extends in a direction away from the active portion of the light intensity measuring device, with a distance between the active portion of the light intensity measuring device and the second end surface of the scintillating fiber being between substantially 15 mm and substantially 200 mm, and wherein a portion of the cylindrical peripheral surface of the scintillating fiber is unshielded from radiation and accessible; wherein radiation measurement is carried out adjacent the accessible portion of the cylindrical peripheral surface of the scintillating fiber; and wherein a cross-sectional dimension of the scintillating fiber is approximately 5 mm.

30. The dosimetry system as recited in claim 19, wherein a cross-sectional shape of the scintillating fiber is generally square.

31. The dosimetry system as recited in claim 29, further comprising an attachment piece which is fixed to the rigid structure and which includes an opening therein adjacent the accessible portion of the cylindrical peripheral surface of the scintillating fiber for receiving and positioning a multi-seed holder relative to the scintillating fiber during radiation measurement.

32. A dosimetry system for measuring radiation for medical applications comprising:

a rigid structure;

a scintillating fiber mounted on the rigid structure in a substantially relatively immovable manner, the scintillating fiber having a cylindrical peripheral surface and first and second end surfaces;

a light intensity measuring device attached to the rigid structure in a substantially relatively immovable manner;

coupling means for optically coupling the first end surface of the scintillating fiber to an active portion of the light intensity measuring device;

means for shielding the scintillating fiber from ambient light;

wherein the light intensity measuring device produces an output signal in accordance with an amount of light generated by the scintillating fiber;

wherein the scintillating fiber is mounted on the rigid structure in such a manner that a longitudinal axis of the scintillating fiber extends in a direction away from the active portion of the light intensity measuring device, with a distance between the active portion of the light intensity measuring device and the second end surface of the scintillating fiber being between substantially 15 mm and substantially 200 mm, and wherein a portion of the cylindrical peripheral surface of the scintillating fiber is unshielded from radiation to be measured and accessible; wherein radiation measurement is carried out adjacent the accessible portion of the cylindrical peripheral surface of the scintillating fiber; and wherein the rigid structure is a rigid bed, and wherein the scintillating fiber is disposed within a groove on the rigid bed.

33. The dosimetry system as recited in claim 21, wherein means are provided for coupling the second end surface of the scintillating fiber with an additional, flexible scintillating fiber, and wherein radiation measurement is additionally carried out using the additional, flexible scintillating fiber.

34. The dosimetry system as recited in claim 32, wherein the light intensity measuring device comprises a battery-powered photomultiplier tube.

35. The dosimetry system as recited in claim 34, wherein a cross-sectional dimension of the scintillating fiber is approximately 5 mm.

36. The dosimetry system as recited in claim 34, further comprising an attachment piece which is fixed to the rigid structure and which includes an opening therein adjacent the accessible portion of the cylindrical peripheral surface of the scintillating fiber for receiving and positioning a multi-seed holder relative to the scintillating fiber during radiation measurement.

37. A compact dosimetry system for measuring radiation for medical applications, comprising:

a rigid bed having a length of between about 75 mm and 260 mm;

a scintillating fiber mounted in a groove on the rigid bed in a substantially relatively immovable manner, the scintillating fiber having a cylindrical peripheral surface and first and second end surfaces;

a photomultiplier tube attached to a tail portion of the rigid bed in a substantially relatively immovable manner;

an optical fiber adapter which is fixed to the photomultiplier tube and which snugly receives a portion of the cylindrical peripheral surface of the scintillating fiber adjacent to the first end surface thereof, the optical fiber adapter optically coupling the first end surface of the scintillating fiber to an active face of the photomultiplier tube; and means for shielding the scintillating fiber from ambient light;

wherein the photomultiplier tube produces an output signal in accordance with an amount of light generated in the scintillating fiber;

wherein the scintillating fiber is supported on the rigid bed in such a manner that a longitudinal axis of the scintillating fiber extends in a direction away from the active face of the photomultiplier tube, with the second end surface of the scintillating fiber being disposed in a portion of the groove on the rigid bed and with a distance between the active face of the photomultiplier tube and the second end surface of the scintillating fiber being between substantially 15 mm and substantially 200 mm, and wherein radiation measurement is carried out adjacent an accessible portion of the cylindrical peripheral surface of the scintillating fiber.

38. The compact dosimetry system as recited in claim 37, wherein the output signal from the photomultiplier tube is fed through an integrator circuit to an analog-to-digital converter for subsequent input to a digital signal processor.

39. The compact dosimetry system as recited in claim 37, further comprising an attachment piece which is fixed to the rigid structure and which includes an opening therein adjacent the accessible portion of the cylindrical peripheral surface of the scintillating fiber for receiving and positioning a multi-seed holder relative to the scintillating fiber during radiation measurement.

40. The compact dosimetry system as recited in claim 37, wherein a cross-sectional dimension of the scintillating fiber is approximately 5 mm.

* * * * *